United States Patent [19]
Jernoiu

[11] Patent Number: 5,342,287
[45] Date of Patent: Aug. 30, 1994

[54] WATERTIGHT WOUND PROTECTOR

[76] Inventor: Justin Jernoiu, Weststrasse 57, 5600 Wuppertal 1, Fed. Rep. of Germany

[21] Appl. No.: 54,858

[22] Filed: Apr. 28, 1993

[30] Foreign Application Priority Data

May 2, 1992 [DE] Fed. Rep. of Germany ....... 9205982
Sep. 16, 1992 [DE] Fed. Rep. of Germany ....... 9212449

[51] Int. Cl.$^5$ .............................................. A61F 13/00
[52] U.S. Cl. ............................................................ 602/3
[58] Field of Search ................ 602/3, 21, 13, 60, 61, 602/62, 77; 2/69.5, 82, DIG. 5; 383/63, 59, 97, 108, 902; 150/154, 155, 156, 157, 158, 159, 160, 161, 166; 206/440, 811, 315.3, 315.4

[56] References Cited

U.S. PATENT DOCUMENTS

| | | | |
|---|---|---|---|
| 3,741,203 | 6/1973 | Liman | 602/3 |
| 4,036,220 | 7/1977 | Ballasalma | 602/3 |
| 4,098,268 | 7/1978 | Scott | 602/3 |
| 4,346,699 | 8/1982 | Little et al. | 602/3 |
| 4,530,350 | 7/1985 | Brown et al. | 602/3 |
| 4,911,151 | 3/1990 | Rankin et al. | 602/3 |

Primary Examiner—Richard J. Apley
Assistant Examiner—Beverly A. Meindl
Attorney, Agent, or Firm—Herbert Dubno; Andrew Wilford

[57] ABSTRACT

A protector for a wound on a body part has a pouch of waterproof material having at least one open end having an edge and a predetermined width so that the body part with the wound can be inserted into the pouch with the body part extending through the open end and past the edge. An elastic strap has a pair of ends one of which is permanently attached to the pouch adjacent the edge. The strap has a length equal to at least twice the width of the open end. A closure attached to the pouch adjacent the edge can be secured to the strap so that the strap can be wound around the edge to press same against the body part and can be secured to the closure to maintain the edge pressed against the body part.

10 Claims, 3 Drawing Sheets

WATERTIGHT WOUND PROTECTOR

FIELD OF THE INVENTION

The present invention relates to a wound protector. More particularly this invention concerns such a protector used on an injury on an extremity to keep it dry.

BACKGROUND OF THE INVENTION

When a person has an injury such as a burn or a sutured cut it is essential to keep it dry until it is substantially healed and/or the sutures are removed. When the wound is on a hand or foot, this can be done by putting a waterproof bag over the extremity and then taping the mouth of the bag tight to the wrist or ankle, with the tape partly on the edge of the bag's mouth and partly on the adjacent flesh. When the injury is closer to the body, it is possible to fit a waterproof sleeve over the limb and tape it similarly on each side.

Both systems have the considerable disadvantage that the wound protection is usable only once. For reuse the tape must be replaced, which normally ruins the waterproof material, and then the protection must be carefully reconstructed. Furthermore, stripping off the tape can injure the wearer, and the adhesive of the tape can produce a rash on sensitive skin. Clearly this system could stand improvement.

OBJECTS OF THE INVENTION

It is therefore an object of the present invention to provide an improved protection system for a wound.

Another object is the provision of such an improved protection system for a wound which overcomes the above-given disadvantages, that is which can be used to keep a wound on a limb dry and that can be put on and taken off easily.

A further object is to provide such a protector that can be reused.

SUMMARY OF THE INVENTION

A protector for a wound on a body part has according to the invention a pouch of waterproof material having at least one open end having an edge and a predetermined width so that the body part with the wound can be inserted into the pouch with the body part extending through the open end and past the edge. An elastic strap has a pair of ends one of which is permanently attached to the pouch adjacent the edge. The strap has a length equal to at least twice the width of the open end. A closure attached to the pouch adjacent the edge can be secured to the strap so that the strap can be wound around the edge to press same against the body part and can be secured to the closure to maintain the edge pressed against the body part.

This is therefore a very neat unit that can be easily fitted over the injured body part and then sealed in place with the strap. The device can be donned fairly easily with one hand, something that is fairly useful when it is used on a hand. Furthermore the device can be reused many times, making showering less onerous a task for someone whose arm or leg has been injured. It can even be used for animals.

According to the invention the strap is made of an elastomer, preferable polyurethane. The closure can be a pair of interengageable hook-and-barb pads and the strap has opposite faces one of which is provided at the outer end with one of the pads and the other of which is provided intermediate the strap ends with the other pad. Such a fastener can be washed without damaging it.

In accordance with a further feature of the invention the pouch is made of a relatively thick watertight synthetic-resin film and is formed with a relatively thin annularly continuous lip of a watertight synthetic-resin film. This lip is cut back adjacent the inner end of the strap. Thus when the strap is pulled tight, the inevitable folds formed in the pouch where it is folded over at the attachment location will not form leak passages, because the lip is tighter at this location and will effectively block flow into the pouch.

For use on a knee or elbow, the pouch has two such open ends each provided with a respective such strap and closure.

It is also possible for the closure to include a part on the strap formed with a plurality of seat holes and another part spaced therefrom and formed with at least one prong engageable in the holes. It can also include a buckle mounted on the strap intermediate its ends in which case the outer end of the strap is formed to pass through the buckle.

To cushion the wounded body part it can be possible to inflate the pouch. More likely, the pouch is at least partially double-walled and forms a substantially closed and inflatable compartment and it is this compartment that can be inflated.

BRIEF DESCRIPTION OF THE DRAWING

The above and other objects, features, and advantages will become more readily apparent from the following, it being understood that any feature described with reference to one embodiment of the invention can be used where possible with any other embodiment and that reference numerals or letters not specifically mentioned with reference to one figure but identical to those of another refer to structure that is functionally if not structurally identical. In the accompanying drawing.

SPECIFIC DESCRIPTION

As seen in FIGS. 1 through 4, a hand-wound protector comprises a mitten-like pouch 1 formed of a tough and waterproof synthetic-resin film. It has an open end or mouth 2 formed with a lip 3 connected at a seam 3″ to the material of the pouch. The end 2 has a width W (FIG. 4) and the cuff or lip 3 is of somewhat smaller width, being cut back at 3′ at one edge of the pouch 1.

Figure 3:
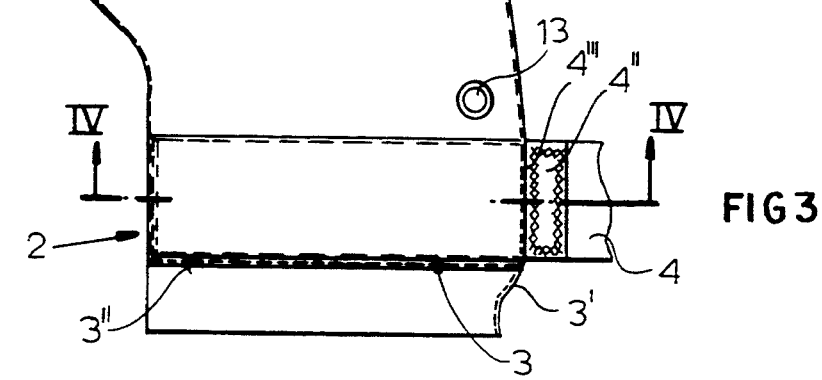
FIG. 3 is a top view of the protector.
Figure 4:
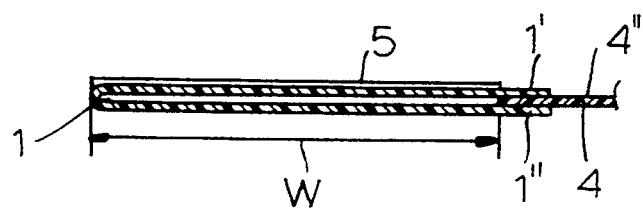
FIG. 4 is a section taken along line IV—IV of FIG. 3.

An elastic strap 4 is attached to the pouch 1 adjacent the cut back portion 3′ of the lip 3 and has an outer end 4′ provided with a closure 6 in the form of a hook tab 6′ somewhat inward of the extreme outer end and a barb tab 6″ at the extreme outer end but on the opposite face of the strap 4. The two closure parts 6′ and 6″ are spaced apart on the strap 4 by a distance equal to about the circumference of the average wrist (or ankle for use on a foot). This strap 4 has an inner end 4" bonded to a tab of a label 5 adhered to the pouch 1 immediately adjacent its open end at the cut-back region 3'. In particular as seen in FIG. 3 the two faces 1' and 1" of the pouch 1 are extended and sandwich the inner end 4" of the strap 4, forming a very solid connection.

This protector is installed by pulling the pouch 1 over the injured hand. The lip 3 automatically slides snugly around the wrist. Then the strap is wound over the mouth end of the pouch 1 and the two closure parts 6' and 6" are pressed together. The folds inevitably formed at the region where the strap end 4" is attached to the pouch 1 are prevented from forming leak zones by the cut-back region 3' of the lip 3, and the strap 4 generally keeps the system tight. It can be removed simply and can be reused many times.

Figure 1:
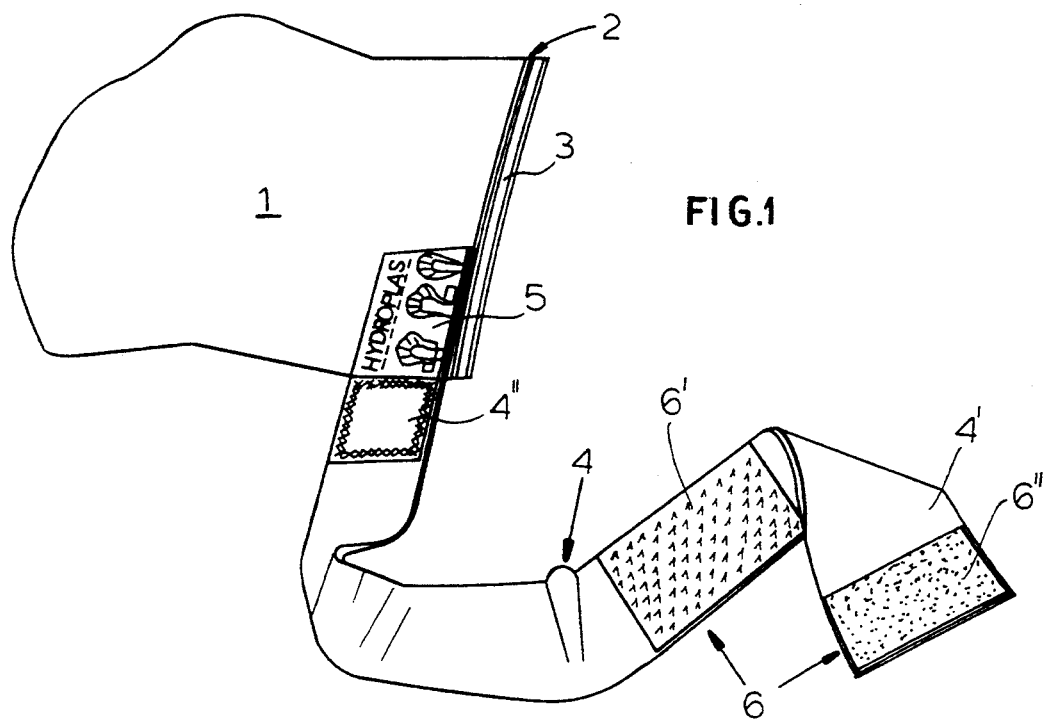
FIG. 1 is a perspective view of a hand-wound protector according to the invention.
Figure 2:
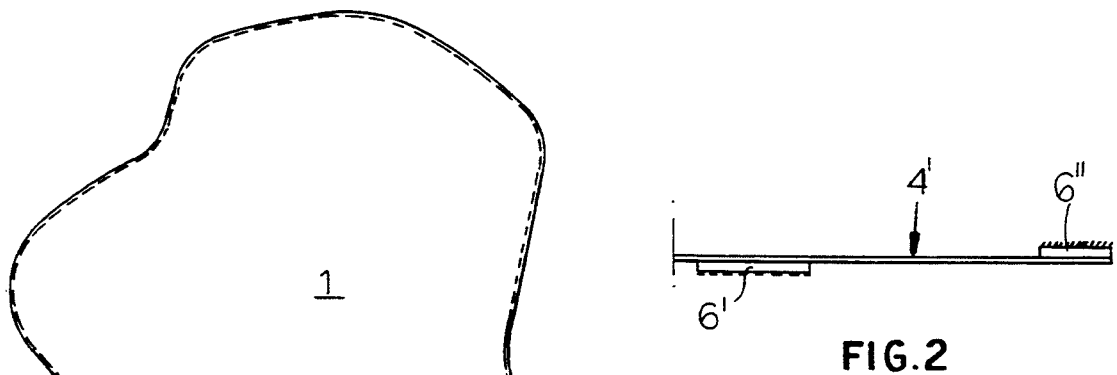
FIG. 2 is a side view of the outer end of the retaining strap.
Figure 9:
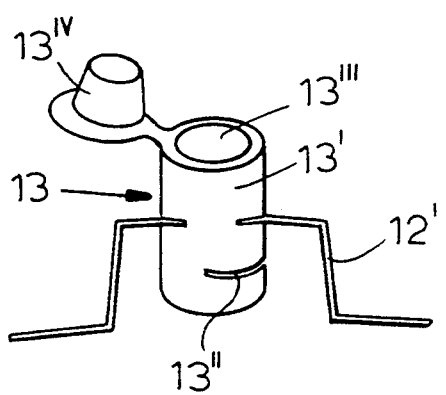
FIG. 9 is a large-scale sectional view through a detail of FIG. 8.

FIG. 1 also shows how the pouch 1 is provided with a connection 13 also shown in FIG. 9 that can be used for inflating it. This connection 13 is a tube 13' traversing a layer 12' of the pouch and having inside the pouch 1 a slit 13" and on the outside a cap 14$^{iv}$ that can block a passage 13''' of the tube 13'. Thus the interior of the pouch 1 can be inflated, or, more likely, a space between inner and outer layers of the pouch 1 to cushion the body part in it. The slit 13" prevents air from leaking out of the connection 13 unless it is pinched.

Figure 5:
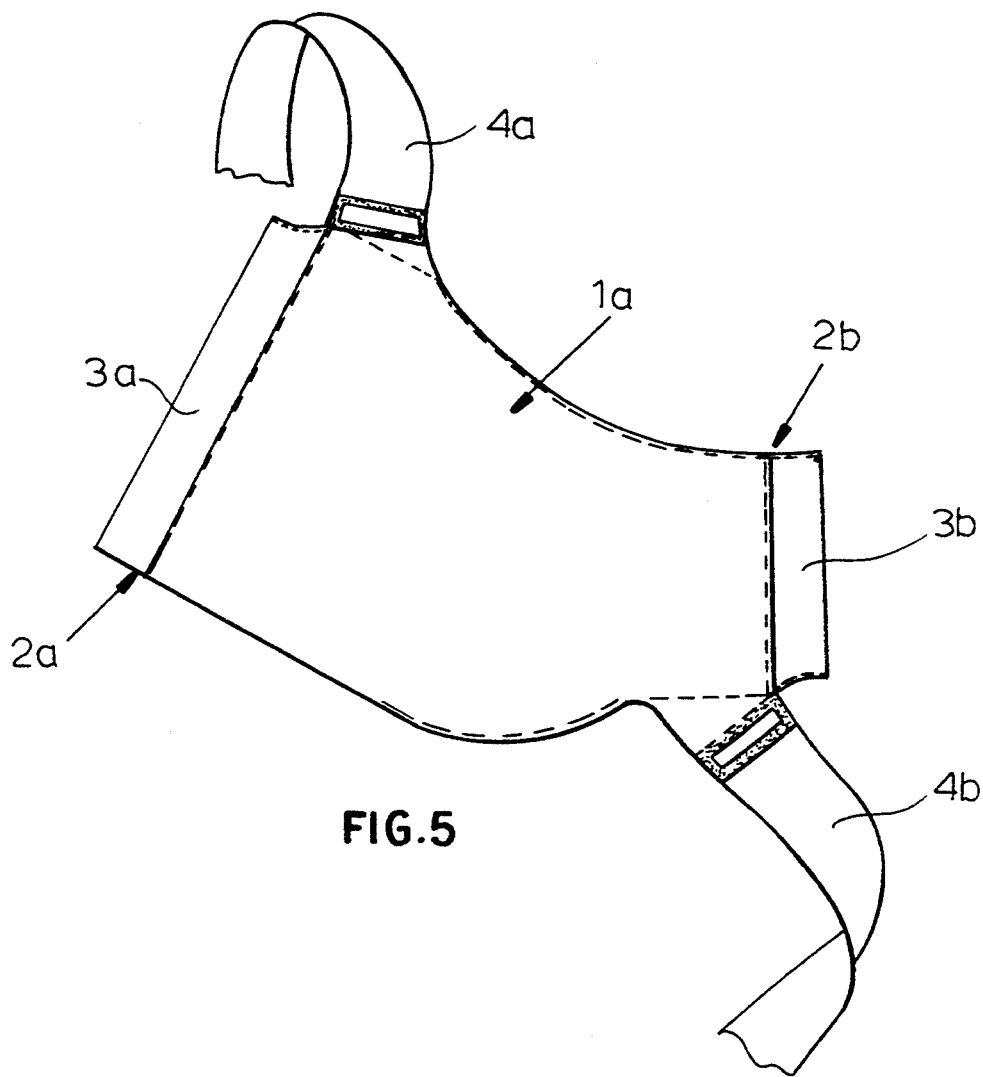
FIG. 5 is a top view of a knee- or elbow-wound protector according to the invention.

FIG. 5 shows an arrangement where a tube 1a replaces the pouch 1 and has two open ends 2a and 2b each provided with a respective lip 3a or 3b and a respective closure strap 4a or 4b. Such an arrangement can be used to keep an elbow or knee injury dry.

Figure 6:
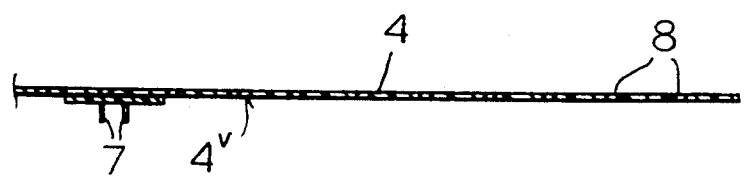
FIGS. 6 and 7 are side and top views of variants of the retaining strap.
Figure 7:
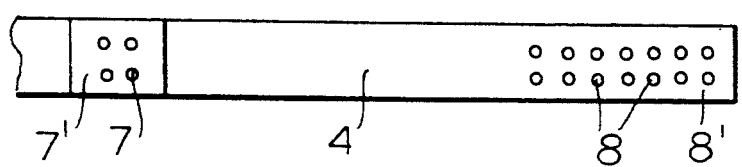

In FIGS. 6 and 7 the strap 4 has on one face a fitting 7' with a plurality of pins 7 and is provided on it opposite face on its outer end with an array 8' of holes 8. The pins 7 are fitted into the holes 8 to form a clasp or closure of the strap 4.

Figure 8:
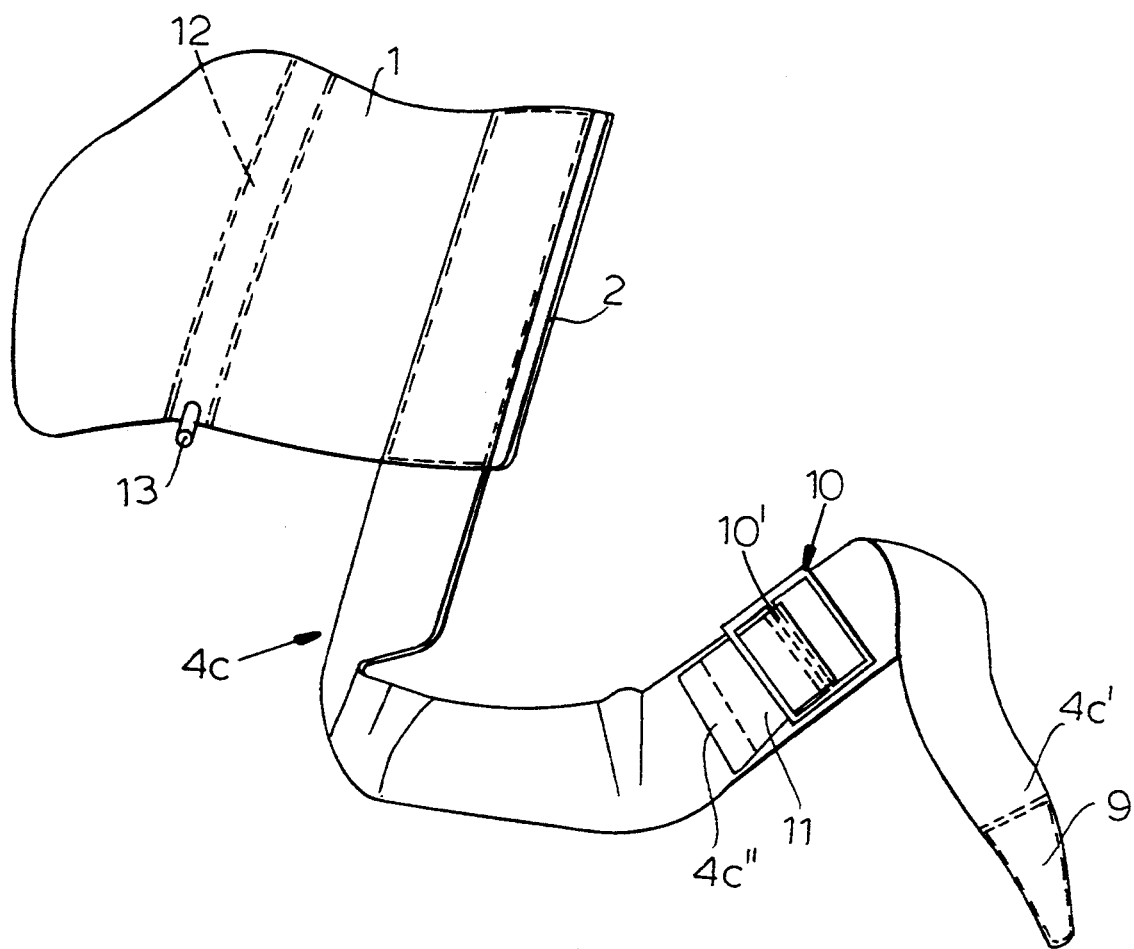
FIG. 8 is a perspective view of another hand-wound protector in accordance with this invention.

The system of FIG. 8 has a strap 4c whose outer end 4'c is formed with a stiffened point 9 and which is provided in its middle with a short connecting strap section 4c" looped around a middle strut 10' of a buckle 10 through which the strap end 4'c can be passed. This system is used like that of FIG. 1, but instead of pressing together the Velcro ™ fastener, the belt end 9 is passed through the buckle 10 and is cinched tight to seal the open end 2.

FIG. 8 further shows how the blow-up connection 13 is provided in an annular zone 12 of the pouch 1. Thus this annular region can be inflated to cushion the hand in the pouch 1, protecting it and gently cradling it.

I claim:

1. A protector for a wound on a body part, the protector comprising:

a pouch of a relatively thick waterproof material having at least one open end having an edge and a predetermined width at the open end, whereby the body part with the wound can be inserted into the pouch with the body part extending through the open end and past the edge, the edge of the pouch being integrally formed with an annular lip of a relatively thin waterproof material;

an elastic strap having
       an inner end permanently attached to the pouch adjacent the edge,
       an outer end,
       a length equal to at least twice the width of the open end, and
       a pair of opposite faces; and a pair of closure parts attached to respective faces of the strap, spaced apart along the strap, and capable of being releasably attached to each other, whereby the strap can be wound around the lip and edge to press the lip and the edge against the body part and can be secured together by means of the closure parts to maintain the edge and lip pressed against the body part.

2. The wound protector defined in claim 1 wherein the strap is made of an elastomer.

3. The wound protector defined in claim 2 wherein the strap is of polyurethane.

4. The wound protector defined in claim 1 wherein the closure parts are a pair of interengageable hook-and-barb pads one of which is provided at the outer end of the strap and the other of which is provided intermediate the strap ends.

5. The wound protector defined in claim 1 wherein the lip is cut back adjacent the inner end of the strap.

6. The wound protector defined in claim 1 wherein the pouch has two such open ends each provided with a respective such strap and closure parts.

7. The wound protector defined in claim 1 wherein one of the closure parts is formed with a plurality of seat holes and the other part is spaced along the strap from the one part and is formed with at least one prong engageable in the holes.

8. The wound protector defined in claim 1 wherein one of the closure parts is a buckle mounted on the strap intermediate its ends, the outer end of the strap constituting the other closure part and being formed to pass through the buckle.

9. The wound protector defined in claim 1, further comprising
    means for inflating the pouch.

10. The wound protector defined in claim 1, wherein the pouch is at least partially double-walled and forms a substantially closed and inflatable compartment, the protector further comprising
    means for inflating the compartment.

* * * * *